US009417192B2

(12) United States Patent
Leuckefeld et al.

(10) Patent No.: US 9,417,192 B2
(45) Date of Patent: Aug. 16, 2016

(54) OPTICAL DEVICE FOR DETECTING QUALITY OF WELDING GUN ELECTRODES

(71) Applicant: FISHER SMITH LLP, Ringstead (GB)

(72) Inventors: Michael Leuckefeld, Dresden (DE); Jens Knobbe, Dresden (DE); Tino Pügner, Dresden (DE)

(73) Assignee: Sinterleghe S.R.L., Turin (IT)

( * ) Notice: Subject to any disclaimer, the term of this patent is extended or adjusted under 35 U.S.C. 154(b) by 0 days.

(21) Appl. No.: 14/771,078

(22) PCT Filed: Aug. 1, 2013

(86) PCT No.: PCT/EP2013/066201
§ 371 (c)(1),
(2) Date: Aug. 27, 2015

(87) PCT Pub. No.: WO2015/014404
PCT Pub. Date: Feb. 5, 2015

(65) Prior Publication Data
US 2016/0131597 A1    May 12, 2016

(51) Int. Cl.
*G01N 21/00* (2006.01)
*G01N 21/95* (2006.01)
*G01N 21/94* (2006.01)

(52) U.S. Cl.
CPC ........... *G01N 21/95* (2013.01); *G01N 21/94* (2013.01); *G01N 2201/0621* (2013.01)

(58) Field of Classification Search
CPC ............ G01N 2035/0036; G01N 2035/00495; G01N 35/00871; G01N 35/026; G01N 35/10; G01N 35/1065; G01N 15/1475; G01N 2015/008; G01N 2015/1486; G01N 2035/00356; G01N 2035/00366; G01N 2035/00425
See application file for complete search history.

(56) References Cited

U.S. PATENT DOCUMENTS

| | | | | |
|---|---|---|---|---|
| 4,491,719 A * | 1/1985 | Corby, Jr. | ............. | B23K 9/0956 219/124.34 |
| 4,711,986 A * | 12/1987 | Lillquist | ................ | B23K 9/296 219/130.01 |
| 2003/0000931 A1* | 1/2003 | Ueda | .................... | B23K 9/0735 219/124.02 |
| 2007/0119829 A1* | 5/2007 | Vietz | ..................... | B23K 26/04 219/121.63 |

* cited by examiner

*Primary Examiner* — Michael P Stafira
(74) *Attorney, Agent, or Firm* — MacMillan, Sobanski & Todd, LLC

(57) ABSTRACT

An optical device for detecting quality of welding gun electrodes An optical sensor device comprises a housing (10) with a pair of openings (11, 11a) communicating with a pair first (14) and a second (15) seat for accommodating a respective one of a pair of electrodes (E1, E2). A first set of lights (16, 17) emit a first (L1) and a second (L2) light beam in an intermediate geometric plane (p1) between the seats (14, 15). Two oblique reflecting elements (25, 26), interposed between the two seats (14, 15), to reflect the first (L1) and second (L2) light beams in two opposite directions perpendicular to the geometric plane (p1) toward the first and the second seats. Other lights (47, 32) emit third (L3) and fourth (L4) light beams on opposite sides of the geometric plane (p1) to illuminate the first and the second seat (14, 15). Cameras (31, 131, 33, 44) capture images (I1, I2) reflected by the two oblique reflecting elements (25, 26) and at least part of the third and fourth light beams (L3, L4) downstream of the first and second seats (14, 15) along paths of the third and fourth light beams.

12 Claims, 7 Drawing Sheets

OPTICAL DEVICE FOR DETECTING QUALITY OF WELDING GUN ELECTRODES

This is a national stage application filed under 35 U.S.C. §371 of international application PCT/EP2013/066201, filed under the authority of the Patent Cooperation Treaty on Aug. 1, 2013. The entire disclosures of all the aforementioned applications are expressly incorporated herein by reference for all purposes.

TECHNICAL FIELD OF THE INVENTION

The present invention relates to an optical sensor device for detecting the conditions of spot welding electrodes.

BACKGROUND ART

It is known that in spot welding plants, with use, the electrodes of the welding guns get worn, deformed and contaminated with metallic residues and oxide deposits. Therefore, the electrodes have to be frequently redressed to regain a clean and proper surface. As known, it is necessary to remove a certain thickness of contaminants that form on the electrode surfaces. The thickness of the contaminant deposit affects the overall electrical and thermal conductivity of the electrode. The shape and size of the electrode, in addition, have a determining influence on the size of the so-called "lens" of the weld. If the electrode tip is too wide, adequate fusion may not be achieved at the interface between the surfaces of the two metal sheets to be welded together.

Typically, when the electrodes exceed a certain size, the operator compensates by increasing the intensity of the electrical current passing through the electrodes. The increased current leads to a number of unfavorable factors. First, the current increase causes an overheating of the cooling liquid and a subsequent enlargement of the welding electrode tips. Overheating causes a reduction of the electrode hardness and a deterioration of its mechanical characteristics. Along with this, a phenomenon known as "mushrooming" occurs, i.e. an increase in the diameter of the electrode and, with it, also the deposition of contaminants.

A need is felt in this technical field to optimize the removal of material deposited on the electrodes. Heretofore, dressing processes have been carried out at regular intervals, according to standardized parameters, concerning the duration of the dressing phase and the clamping force with which the welding gun closes its electrodes on the dressing unit. Standard parameters, in terms of time and force, represent a compromise that is suitable in most cases. However, the removal of material occurs without a knowledge of the exact thickness of the surface layers of electrodes that should be removed.

Further, dressing has heretofore been carried out in an undifferentiated manner to both the anode and the cathode. Since a greater deposit of contaminants occurs on the cathode, in order to optimize electrode duration and operation, deposits should be removed to a greater extent from the cathode than from the anode.

SUMMARY OF THE INVENTION

Therefore it is a main object of the present invention to know the thickness of the surface layers to be removed, in order to perform the dressing in an optimized manner, that is, adjusting the dressing time (for example, 3 milliseconds) with a predetermined pressure (for example 150 daN), so as to remove only the oxide deposits and save the material of the electrodes which is still uncontaminated.

Dressing optimization prolongs the useful life of the electrode. Consequently, this involves a reduction of the idle time required for stopping a production line in order to replace the worn electrodes. A standstill of a line involves an economic loss, which sometimes may even be unnecessary in case the electrodes do not really need to be redressed or replaced.

A need is also felt to keep welding parameters constant and, particularly, the intensity of current which is applied and the closing and welding time the welding gun, so that these parameters are always correct and in compliance with optimized standards. Above all, one should avoid the risk that an inappropriate change in the intensity of current or in the duration of the current application causes defective welds. Another object of the invention, therefore, is to prevent or reduce the need for servicing in order to set the right welding parameters (current, time).

A reduction in the number of manual operations is also beneficial, as it reduces the risk of accidents. Therefore, a further object of the invention is to increase safety for the personnel working on a welding line.

A further object of the invention to reduce power consumption of the welding line, as well as a reduction in $CO_2$ emissions.

Another object of the invention is to certify the weld quality. Currently, the quality controls of modern welding systems are only able to certify that the welds were created in compliance with certain parameters (current intensity, time and force or pressure of closing of the welding gun). But a variation of electrode condition, caused by normal wear and contamination cannot be detected. Electrode condition is a major factor influencing weld quality and consequently frequent destructive tests of weld must be carried out. The invention is able to monitor and repair electrode shape and surface condition, enabling the motor vehicle manufacturers to certify all major process factors that can influence weld quality. This affords greater confidence in the reliability of the welding process and enables a reduction in the frequency of destructive tests.

A further object of the invention is to provide a useful tool to certify that the welding points have been applied according to certain welding parameters (intensity of current applied, application time of the current, clamping force or pressure applied by the welding gun) and with electrodes having an optimal geometric shape. A quality certification may allow a reduction in the total number of welding spots applied to a given welded assembly, due to the welds being certified. Currently, the production of a motor vehicle requires 5000 to 6000 welding points. Since welding points are not certified, a rather high percentage of additional welding points are required for safety reasons.

A still further object of the invention, therefore, is to reduce the number of welding points, as well as time and costs that this entails.

Another object of the invention is to allow the selection of the most appropriate dressing tool, i.e. more or less aggressive, depending on the level of degradation of the electrodes.

The above and other objects and advantages, which will be better understood hereinafter, are achieved according to the present invention by a sensor device having the features defined in the appended claims. In summary, the sensor device is based on an optical reflection system, which illuminates the tip faces of the electrodes and takes measurements of both reflectivity and the area/shape of the tip surface. In this way, tip face diameter and material condition, which are the two key parameters determining the quality of the weld, will be assessed. The sensor device will generate, through a CPU, a quantitative measure of the quality electrode, preferably in the form of a percentage, on a scale between a fully clean and required tip face diameter, to a black or worn or excess diameter, which is a condition not capable of meeting weld quality requirements. This information will likely be relayed to and used by a control system for controlling a tip dress schedule. The same information may also be used to assess the rate of degradation or wear of the abrasive tooling. An appropriate kind of tool may be chosen as a function of the degradation status. A more or less aggressive kind of tooling (milling cutter) may be chosen accordingly. The sensor device may be conveniently located near a dresser unit. The sensor device will assess quality electrode tip dressing immediately after, or even before dressing.

BRIEF DESCRIPTION OF THE DRAWINGS

The features and advantages of the invention will become apparent from the ensuing detailed description of a few preferred, but not limiting, embodiments thereof. Reference is made to the accompanying drawings, in which.

DETAILED DESCRIPTION

Figure 1:
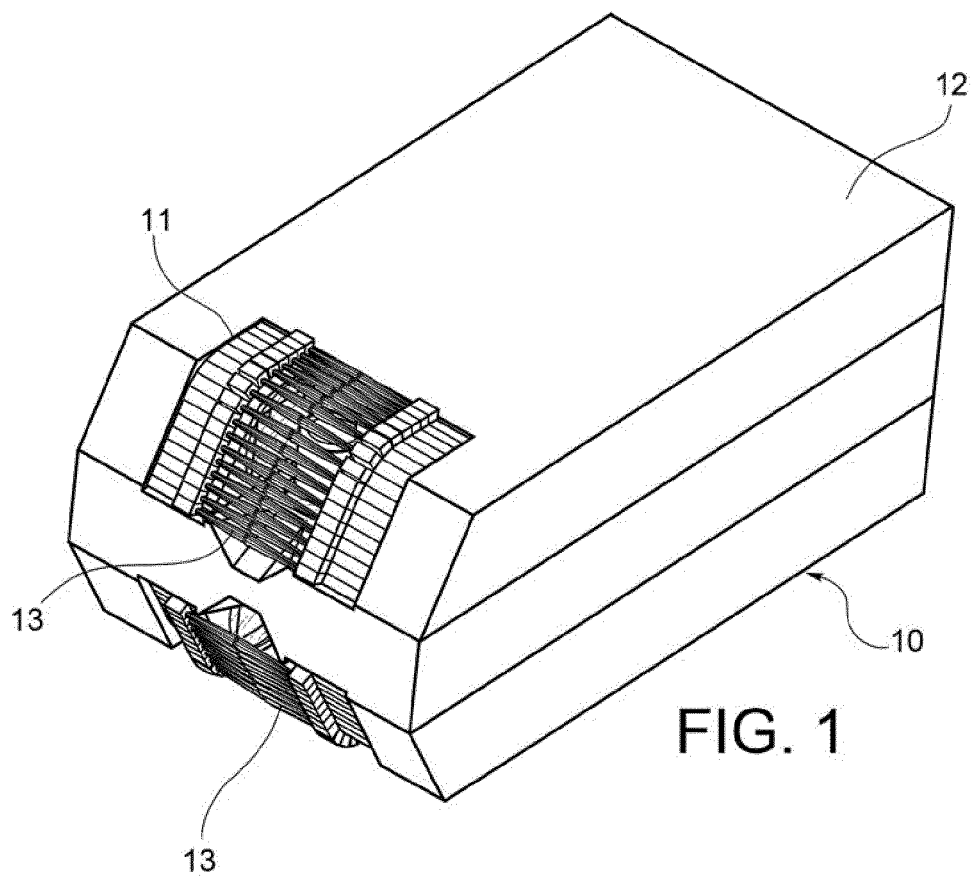
FIG. 1 is a perspective view schematically illustrating a housing of an optical sensor device.
Figure 2:
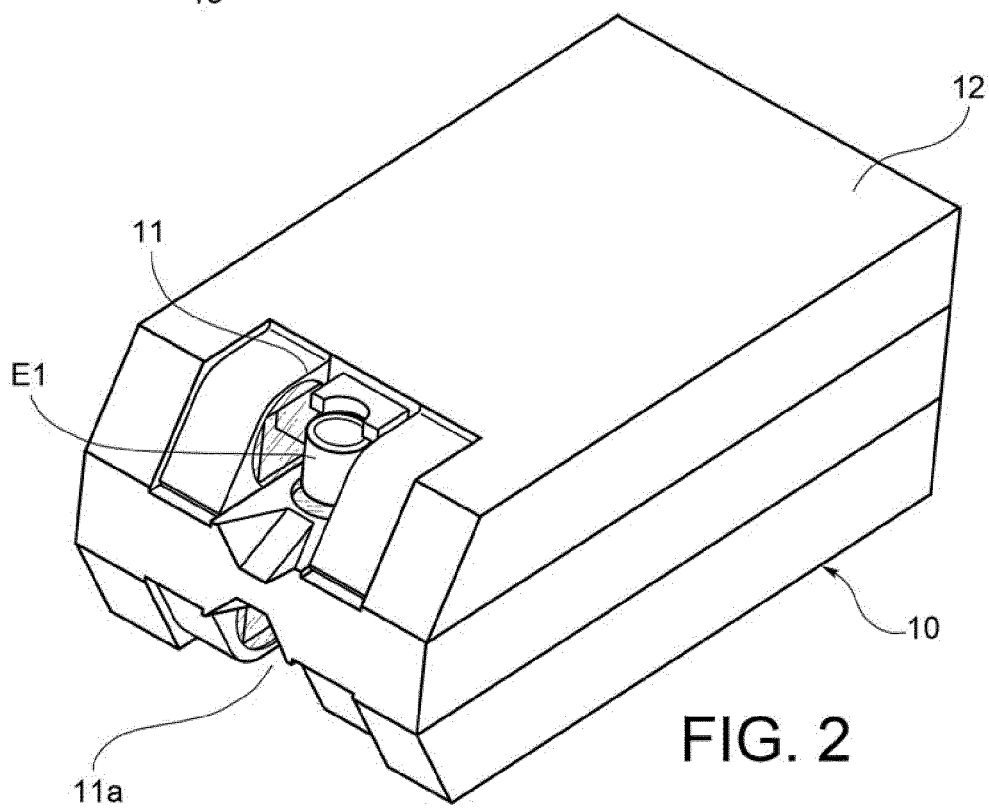
FIG. 2 is a perspective view of the housing of FIG. 1, where some parts have been removed for illustrative purposes.

Referring initially to FIGS. 1 and 2, numeral 10 designates in its entirety a housing of an optical sensor device according to an embodiment of the invention. The optical sensor device is designed to detect images of a pair of spot welding electrodes carried by a welding gun. Welding guns are generally known, and therefore will not be described nor illustrated.

The housing 10 has a pair of openings 11, 11a, formed in this example on two different sides of the housing. Two electrodes E1, E2 carried by a welding gun (not shown) may be introduced in the device through the openings 11. Only one of the openings 11 is visible in FIGS. 1 and 2; a similar opening 11a is formed in the side of the housing opposite to side 12.

In order to prevent the entrance of light, dust and other impurities within the housing 10, the openings 11, 11a are equipped with brush stripes 13. In FIG. 2 the brush stripes 13 have been removed only for illustrative purposes.

A pair of seats or measurement places 14, 15, separated from each other, are provided inside the openings 11, 11a of the housing. Each seat 14, 15 is configured to receive a respective one of a pair of electrodes E1, E2 carried by a welding gun. The electrodes, once docked on the measurement places, are illuminated in the following way to capture images of their front and side faces.

Figure 3:
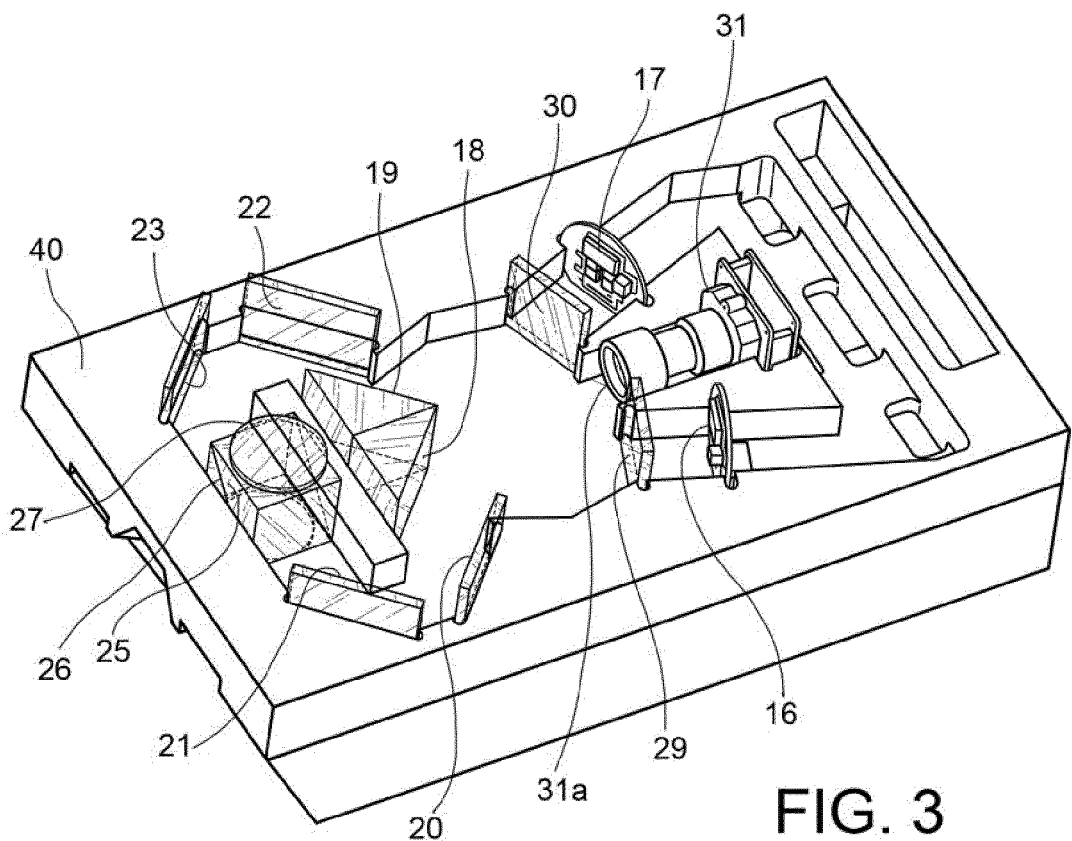
FIG. 3 is a perspective view of some inner parts of the sensor device, particularly a supporting plate with optical components for illuminating and obtaining images of the front faces of a pair of electrodes.
Figure 5:
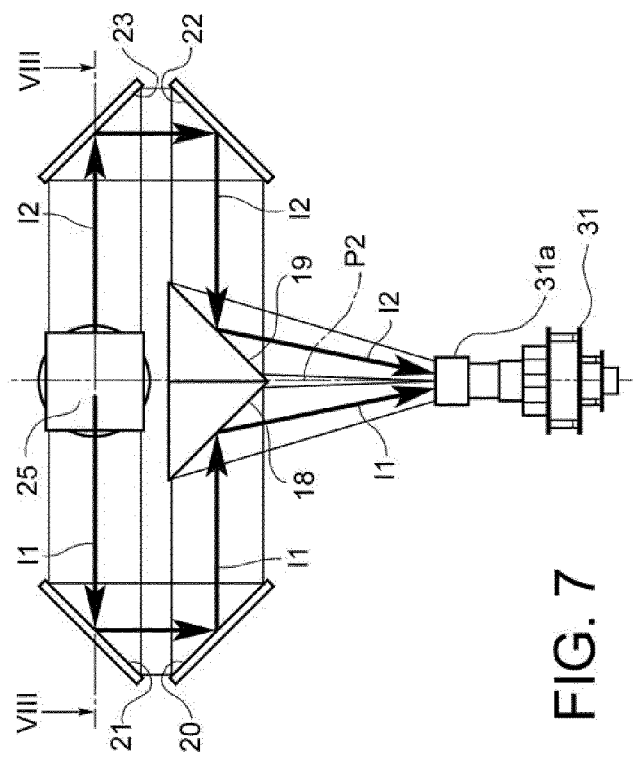
FIG. 5 is a plan view schematically illustrating the light paths of a pair of light beams which illuminate the front faces or tips of a pair of electrodes.

The tips or front faces of the electrodes are illuminated using, in the example of FIGS. 3 and 5, a pair of light sources 16, 17, preferably LED light sources, and a plurality of reflecting surfaces.

The LED light sources 16 and 17 project light beams L1 and L2 which illuminate two optical diffusors 29 and 30 with a certain wavelength. The wavelength depends on the material combination between electrode and the welded metal sheets, to achieve optimal contrast of the contaminations on the electrode. The optical diffusor is preferably opal glass, due to its capability to shape the locally uneven beam profile intensity of the LED to a nearly perfect diffused (evenly distributed) beam profile intensity. This is necessary to achieve an equally illumination of the electrode front for measurements.

Figure 6:
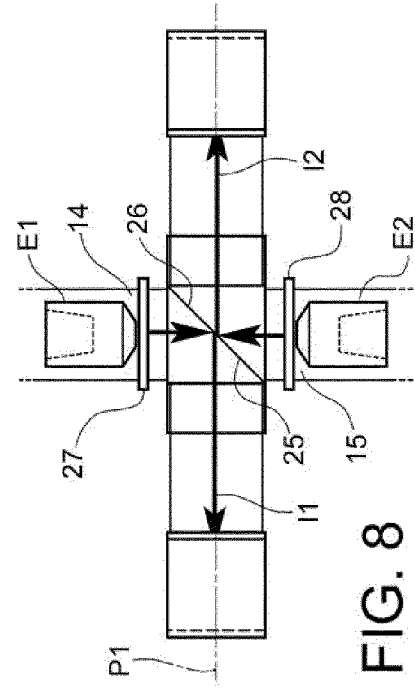
FIG. 6 is a schematic, vertical cross-sectional view taken along line VI-VI of FIG. 5, showing vertical parts of the light paths for illuminating the front faces of the electrodes.

The now diffuse light beams L1 and L2 are oriented in an intermediate geometrical plane p1 between the two seats or measurement places 14, 15. The light beams L1 and L2 are reflected from a set of front mirrors to the optical elements 24 and 25, as shown in FIGS. 5 and 6. In this example, mirrors 18 and 19 are triangular front mirrors and 20 to 23 are flat front mirrors.

The two light beams L1 and L2 converge on two respective obliquely reflecting optical elements 25 and 26. These elements are interposed between the two seats 14, 15 in which the electrodes E1, E2 are received (FIG. 6). According to a preferred embodiment, the optical elements 25 and 26 are agglutinated rectangular prisms with reflective coated hypotenuses which extend in geometric planes which are skewed with respect to the intermediate geometrical plane p1. Due to this arrangement, the optical elements 25 and 26 reflect the light beams L1 and L2 perpendicularly to the geometric plane p1 in opposite directions, towards the front faces or tips of the electrodes E1, E2.

The two oblique reflecting elements 25, 26 reflect the first and second light beams L1 and L2 in two opposite directions first and the second seat, where these beams hit the front faces or tips of the electrodes E1, E2.

The electrodes E1 and E2 are docked onto optical windows 27 and 28, which determine the positions and partly form the seats or measurement places and protect the optical system. Conveniently, the optical windows 27 and 28 are sapphire windows, sustained by the housing 10. These windows provide accurately located supporting points and abutments for the electrodes. Sapphire windows are preferred, since they are scratch resistant and mechanically strong enough to withstand the full closing force of a welding gun (approximately of 3.5 kN, 1.75 kN per window).

Figure 7:
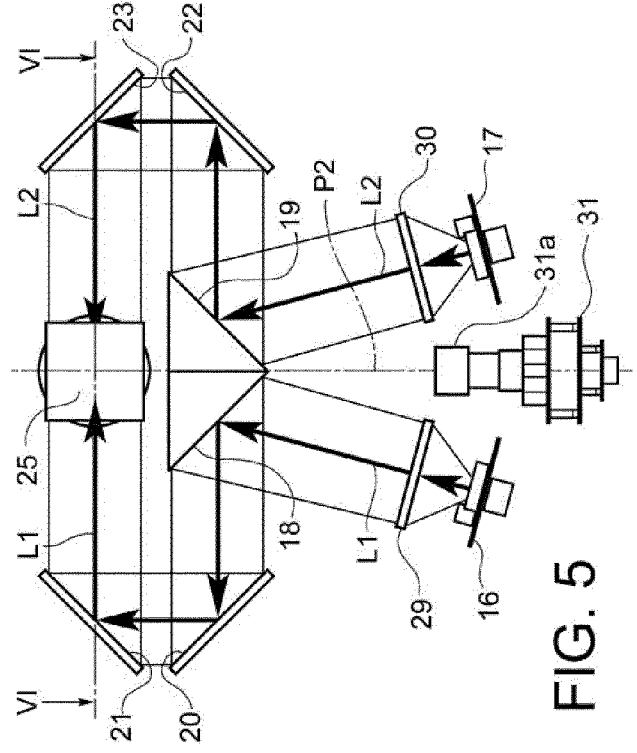
FIG. 7 is a schematic view illustrating optical paths of images of the front faces of the electrodes.
Figure 8:
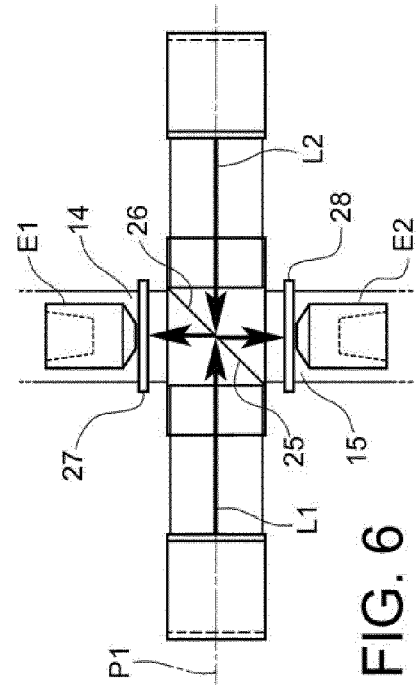
FIG. 8 is a schematic cross-sectional view taken along on the line VIII-VIII of FIG. 7, showing the vertical part of optical paths followed by images of the front faces of the electrodes.
Figure 10:
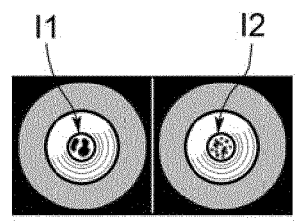
FIG. 10 are pictures, as taken by a camera, of the front faces or tips of the electrodes.

The light beams L1 and L2, incident on the front faces of the electrodes, produce respective images I1, I2 that follow a reverse path between the mirrors, as depicted schematically in FIG. 7. These images are captured by an image recording means, in this embodiment a camera 31 with an objective 31a. As schematically shown in FIG. 10, the front images I1, I2 provide information on the wear and cleanness conditions of the electrode tips, as well as of their diameter. The front faces of the electrodes are illuminated using substantially the same optical path as that of the images of the electrodes returning to the camera 31 and camera objective 31a, as shown in FIGS. 3, 5 and 7.

According to a particularly compact embodiment, the light beams L1, L2 and the light sources 16, 17 are arranged symmetrically, on opposite sides of a symmetry plane p2 in which the camera 31 is located and oriented. The available space is further optimized by arranging the sets of reflecting surfaces 18-26 in such a way as to create two luminous paths according to a closed polygonal line (in this example according to a rectangle, FIGS. 5 and 7) thus reaching the two oblique reflecting elements 25, 26 which divert the two light beams on each of the front faces of the electrodes.

The optical components illustrated in FIG. 3 (light sources 16, 17, reflecting surfaces 18-26 and camera 31) can be mounted on an intermediate support frame 40 which embraces the intermediate geometric plane p1. According to an advantageous embodiment, the support frame 40 forms a plurality of seats and recesses for mounting said components in predetermined positions.

Although the embodiment illustrated in FIG. 3 provides a single camera 31 adapted to capture images of the front faces of both of the two electrodes, according to other embodiments two separate cameras may be used, each intended to capture images of one of the electrode front faces.

Figure 12:
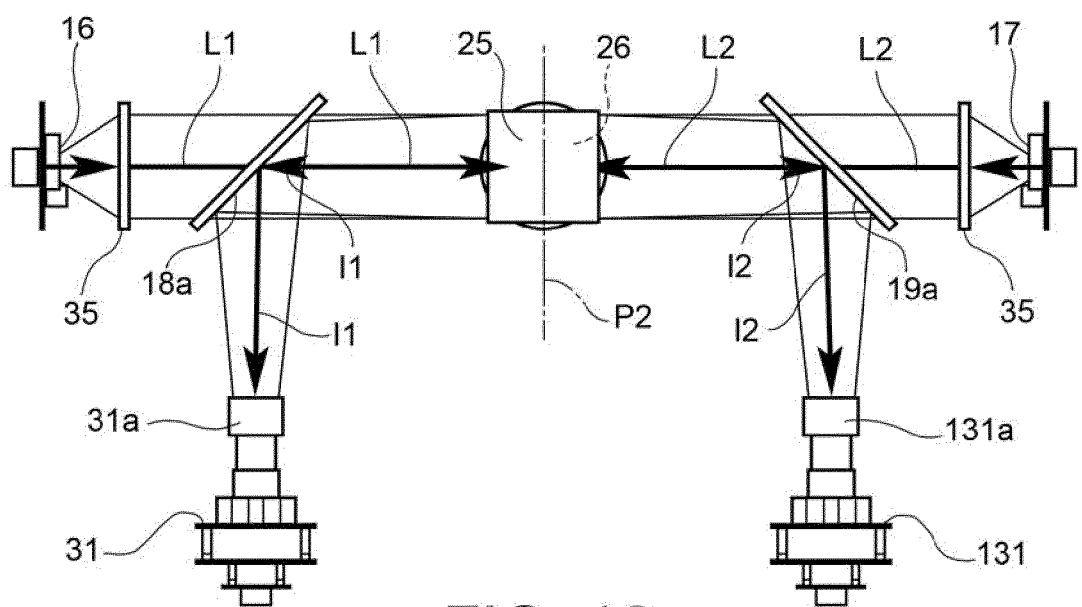
FIG. 12 is a schematic plan view of an optical system capable of obtaining images of the front faces of a pair of electrodes, according to an alternative embodiment of the invention.
Figure 13:
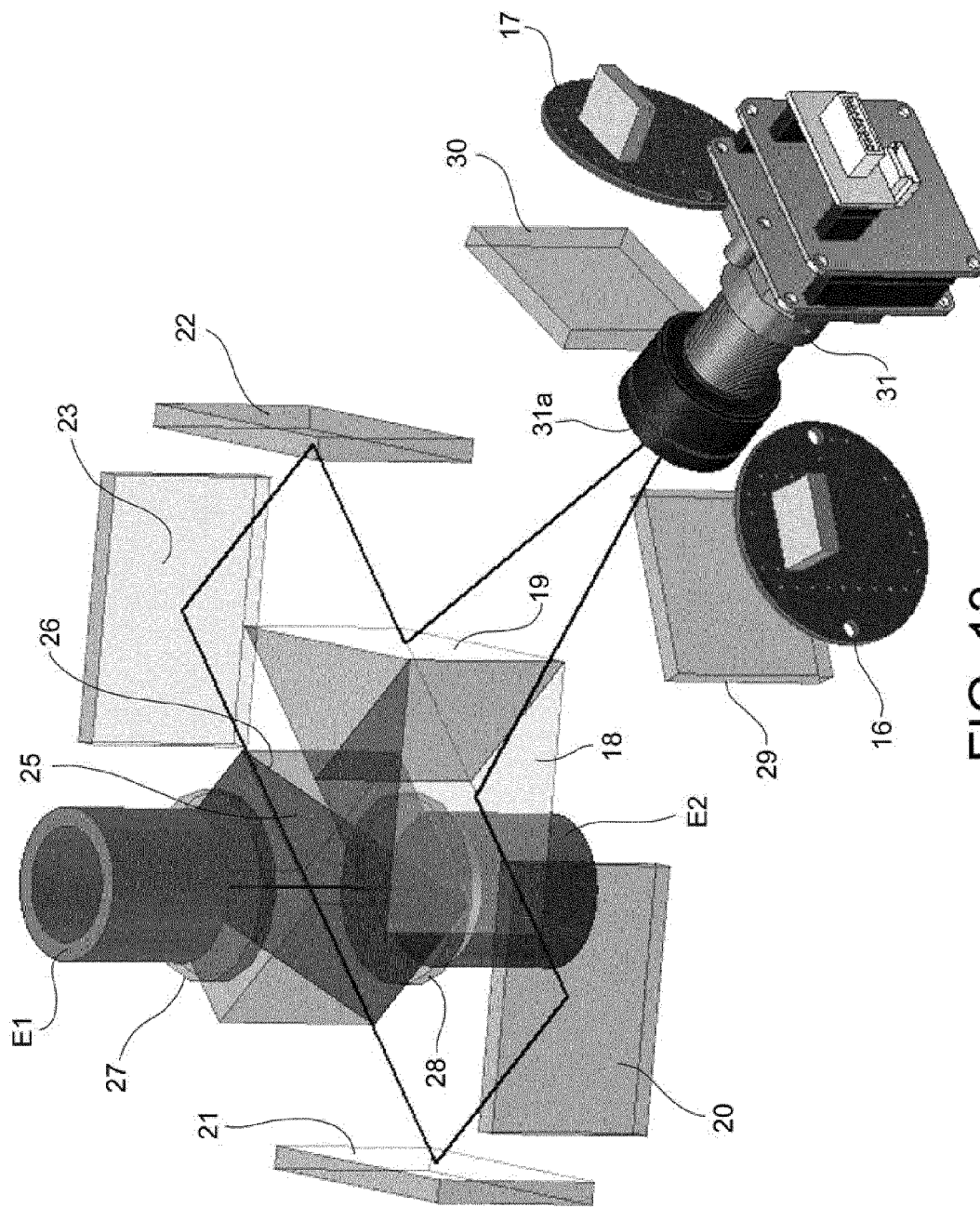
FIG. 13 is a perspective view illustrating the working principle for taking images of the front faces or tips of the electrodes.

An exemplary, alternative embodiment, providing two distinct cameras 31, 131, is schematically shown in a plan view in FIG. 12. According to FIG. 12, for illuminating the front faces of the electrodes, two light sources 16, 17 project a respective pair of light beams L1 and L2 in a geometric plane intermediate between the electrode seats or measurement places 14, 15. In this example, the two oblique reflecting elements 25, 26 are placed in an intermediate position between the two light sources 16 and 17. The two beams L1, L2 emitted from these sources are aligned and directed toward one another, in a direction substantially perpendicular to the symmetry plane p2. Between each of the light sources 16, 17 and the oblique reflecting elements 25, there is interposed a respective partially transparent reflecting element 18a, 19a. This leaves the respective light beam L1, L2 coming directly from the source 16, 17 filter towards the respective oblique reflecting element 25, 26 and reflects the front image I1, I2 of the respective electrode E1, E2, coming from the same oblique reflecting element 25, 26 deflected in the plane p1 towards a respective camera 31, 131. The locations of the cameras, as well as the angles of deflection and reflection of the light beams and the electrode images, are not to be construed as limiting.

Figure 4:
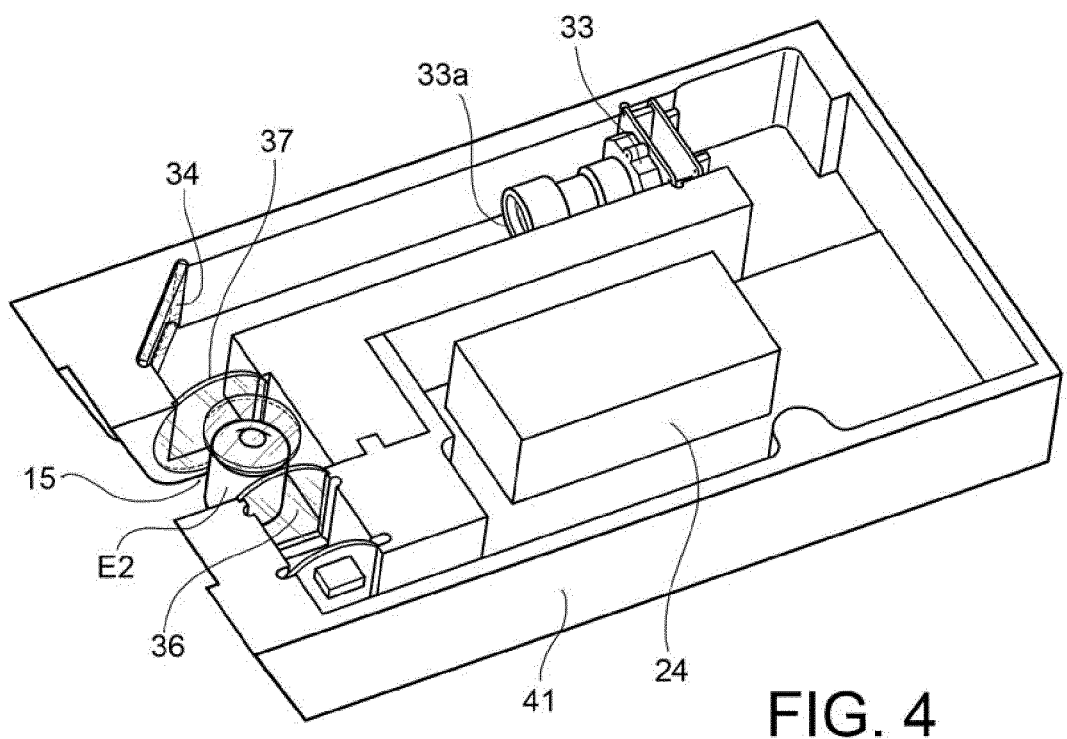
FIG. 4 is a perspective view schematically illustrating other inner parts of the sensor device, particularly a supporting plate with optical components for illuminating and obtaining a side view of one of the electrodes.
Figure 9:
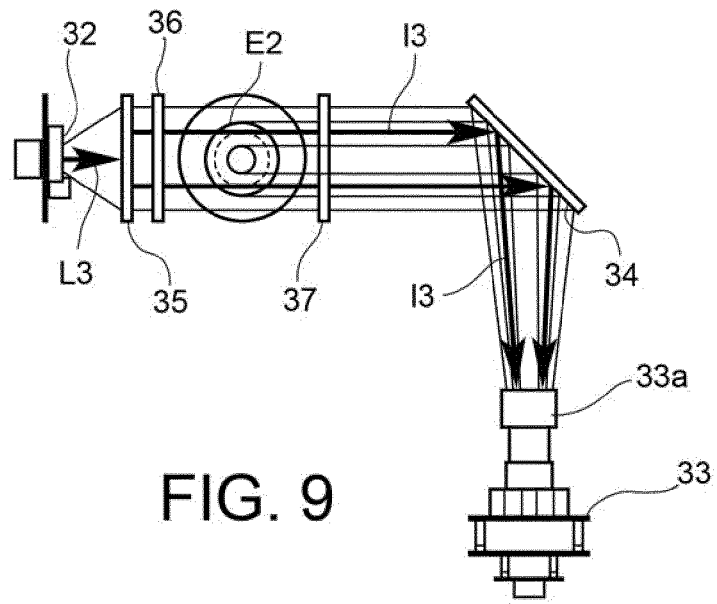
FIG. 9 is a schematic plan view of the path of a light beam that illuminates a side surface of one of the electrodes.

FIGS. 4 and 9 show one of two assemblies adapted to generate and capture side images of one of the electrodes, in this example lower electrode E2.

Figure 11:
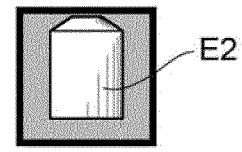
FIG. 11 is a picture, as taken by a camera, showing a side view of an electrode.

A third light source 32 is used to emit a third light beam L3 to illuminate a side of the electrode E2 accommodated in the lower seat 15. A central part of the third light beam is obscured by the electrode E2, while a peripheral part 13 of this beam is captured by an image recording means 33, in this embodiment a camera with an objective 33a. That peripheral part of the third light beam that passes beyond the electrode E2 generates an image which is indicative of the size and shape of the contour of the electrode, and therefore of its condition of wear (FIG. 11).

In the embodiment shown in FIGS. 4 and 9, in order to optimize the available space within the housing, the third light beam L3 follows an angled or non-rectilinear path, being deflected by a reflecting surface 34. The third light beam L3 crosses an optical diffusor 35, in this embodiment opal glass, plus two sapphire windows 36 and 37. These are mounted on either side of the electrode E2, to protect the optical system.

The components 32-37 shown in FIGS. 4 and 9 may be mounted on a lower support frame 41 preferably having a plurality of seats and recesses for fitting those components accurately in predetermined positions. The support frame 41 may be secured under the intermediate frame 40 within the housing 10.

Figure 14:
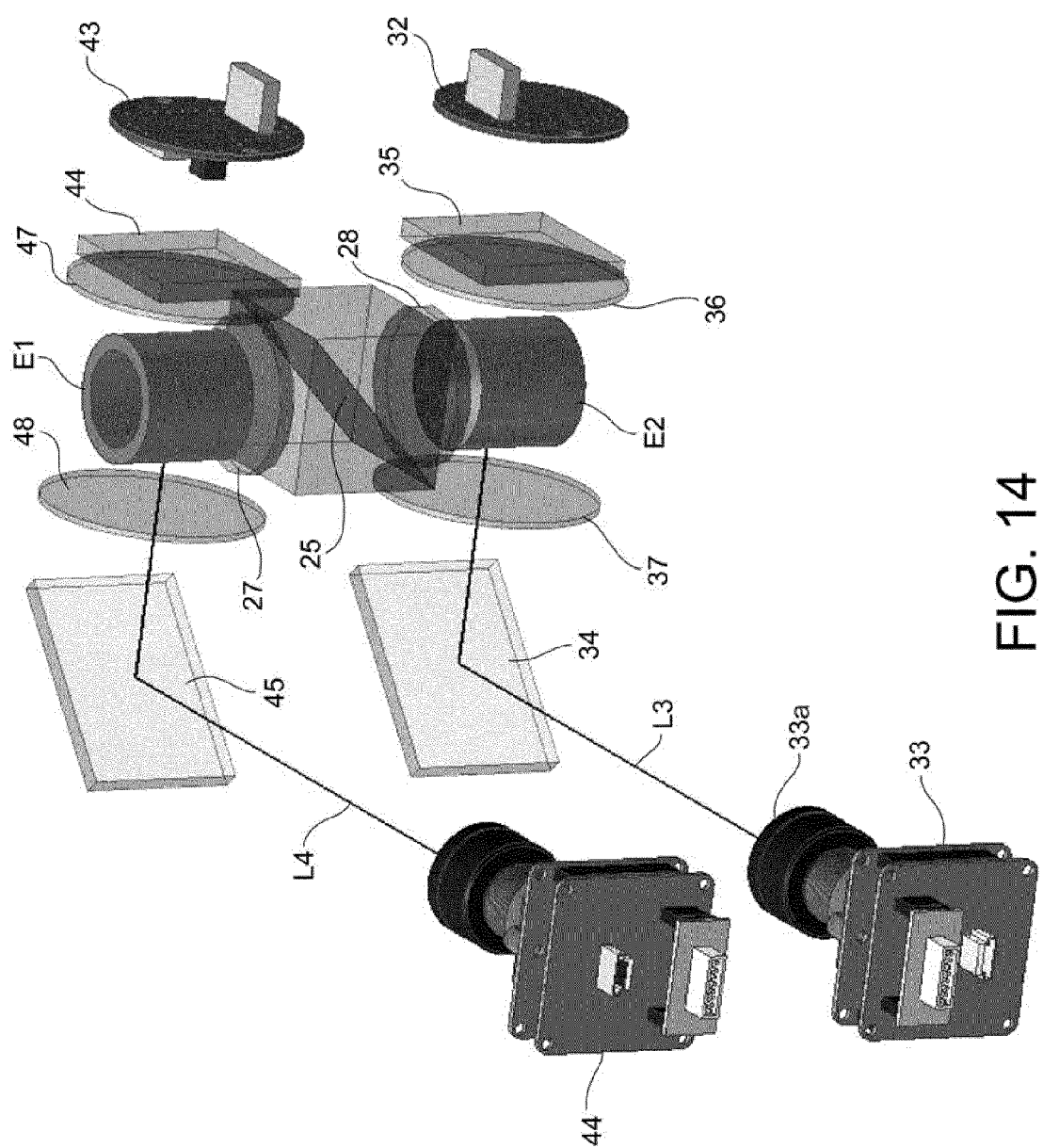
FIG. 14 is a perspective view illustrating the working principle for taking images of the sides of the electrodes.
Figure 15:
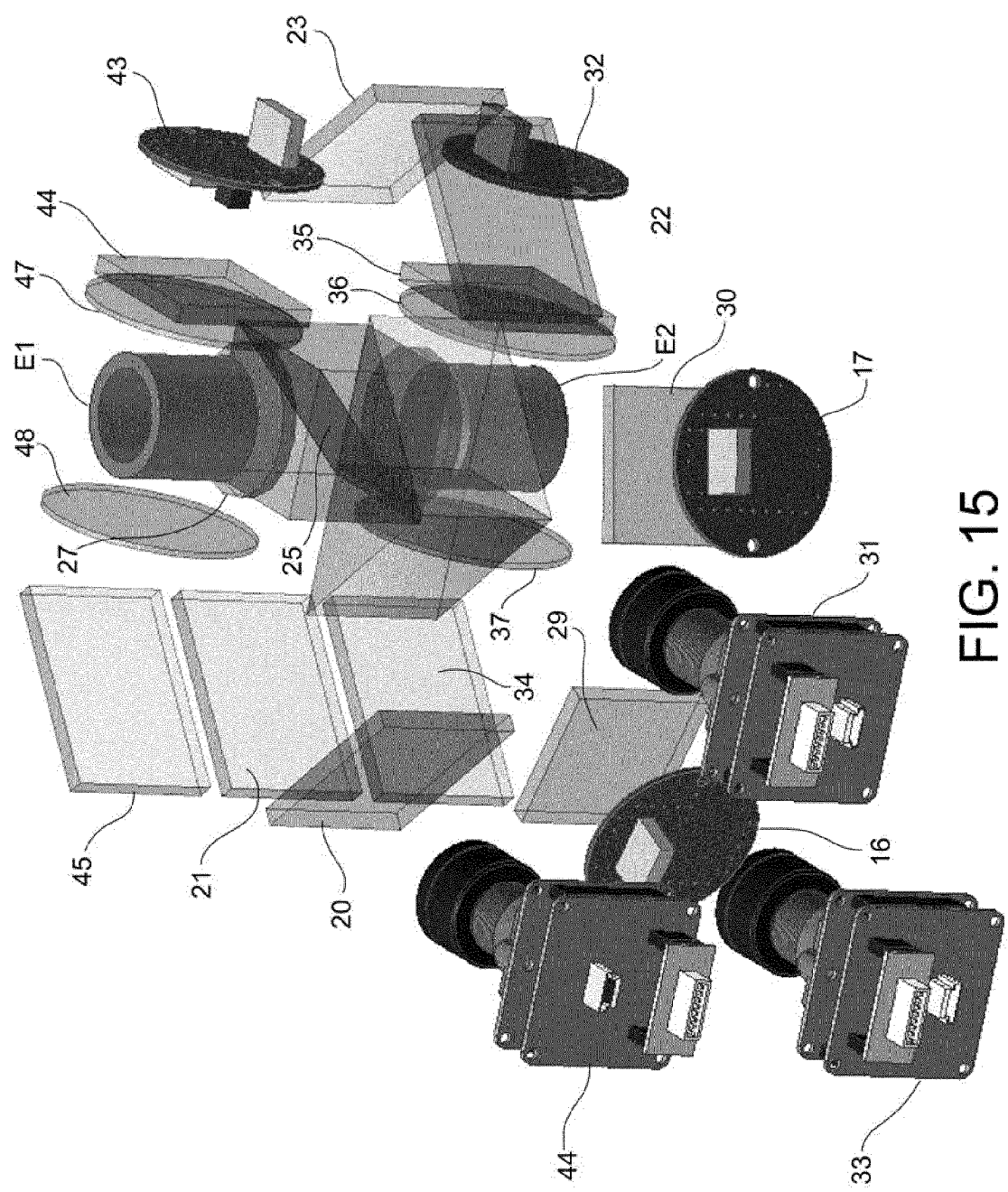
FIG. 15 is a perspective view illustrating the working principle for taking images of the front faces and the sides the electrodes.

According to a preferred embodiment, a second assembly, identical to the one shown in FIGS. 4 and 9, is designed to generate and capture side images of the upper electrode E1. The second assembly (visible in FIG. 14) includes a fourth light source 43 emitting a fourth light beam L4 to illuminate a side of the electrode E1 located in the upper seat 14. A central part of the fourth light beam is obscured by the electrode E1, while a peripheral part 14 of this beam, which passes around and beyond the electrode E1, is captured as an image from an image recording means 44, such as a camera or video camera.

Similarly to the assembly shown in FIG. 4, and according to a substantially identical planimetric arrangement, the fourth light beam L4 may follow a non-rectilinear path deflected by a reflecting surface 45. Along the path of the fourth light beam L4 there may be fitted an opal glass 44 immediately downstream of the fourth light source 43 as well as two sapphire windows 47, 48 respectively located immediately upstream and downstream of the electrode E2.

According to an embodiment, the components 43-48 may be mounted on a support frame bottom (not shown), similar to the upper frame 41 and having a plurality of seats and recesses for fitting components 43-48 accurately in predetermined positions. The lower support frame may be fixed on top of the intermediate support frame 40 within the housing 10.

In accordance with a further embodiment, all the light beams, namely both those intended to provide images of the front faces, and both those intended to provide information and images of the contour of the electrodes, may originate from a single light source rather than from individual, separate light sources.

Likewise, by suitably rearranging the reflecting surfaces, it is possible to direct all images to a single image recording means, for example, a single camera or video camera, capable of recording images in frames or windows being part of a single overall image.

The sensor device may also incorporate a pneumatic circuit (not shown) to keep those surfaces that come in contact with the electrode permanently clean.

The sensor device may incorporate a CPU 24 (FIG. 4) that is protected from contamination by external elements (dust, heat).

As will be appreciated, the sensor device allows to simultaneously detect overall images of a pair of welding electrodes.

The image of the side view (FIG. 11) provides information concerning the shape of the tip and the height that is left, for the decision to change or to dress the electrode. The side picture also gives information about the electrode wall thickness. The front view (FIG. 10) gives information about the grade of impurity and wear at the contact surface of the electrode caused by the welding process.

According to an embodiment, the light sources may produce red, diffuse light (~650 nm) which gives the best contrast on copper electrodes used for steel sheet welding. Because of the usual purifications there is tin (from the steel sheet tin coating) which forms an intermetallic phase with the copper (bronze) and a carbon deposition (black dust) from the rests of oil on the steel sheets (coming from the cold drawing of the steel sheets). These purifications absorb the red wavelength mostly, while the copper reflects it, so one gets a good contrast between both. There may also be a blue illumination (~470 nm), integrated in the same light source (e.g. 2 blue and 2 red LEDs on the same board), individually controllable. Blue light is used for copper electrodes used to weld sheets of aluminum. In this case the aluminum forms also an intermetallic phase on the surface of the electrode. These purifications have also a high reflectivity, like copper in red wavelengths. So a blue light wavelength is used which reflects better on aluminum than on copper. This blue light is mostly absorbed on copper, but reflected by aluminum. As a result, the picture of aluminum purifications shows bright areas of dirt and dark areas of the copper.

Although LEDs have proven to be the cheapest and most appropriate light sources, other discrete wavelength light sources may be used. For example, a laser of a discrete wavelength may be used as a possible light source, although a laser is more costly and requires special arrangements for beam shaping to a relatively wide area to illuminate.

A number of embodiments and aspects of the invention have been disclosed. It is to be understood that each embodiment may be combined with any other aspect/embodiment. Moreover, the invention is not restricted to the described embodiments, but may be varied within the scope of the accompanying claims and their legal equivalents.

The invention claimed is:

1. An optical sensor device for detecting images of a pair of spot welding electrodes (E1, E2) carried by a welding gun, the device comprising:
    a housing (10) having at least one pair of openings (11, 11a);
    at least a first (14) and a second (15) seat spaced from one another within the housing, each seat communicating with a respective one of the openings (11, 11a), each seat (14, 15) being adapted to accommodate one of the electrodes carried by the welding gun;
    first illuminating means (16, 17) adapted to emit a first (L1) and a second (L2) light beam in an intermediate geometric plane (p1) between the seats (14, 15);
    two oblique reflecting elements (25, 26), interposed between the two seats (14, 15), the oblique reflecting elements being adapted to reflect the first (L1) and second (L2) light beams in two opposite directions perpendicular to the geometric plane (p1) toward the first and the second seat;
    second illuminating means (47, 32) adapted to emit third (L3) and fourth (L4) light beams on opposite sides of said geometric plane (p1) to illuminate the first and the second seat (14, 15);
    image recording means (31, 131, 33, 44) adapted to capture images (I1, I2) reflected by the two oblique reflecting elements (25, 26) and at least part of the third and fourth light beams (L3, L4) downstream of the first and second seats (14, 15) along paths of the third and fourth light beams.

2. An optical sensor device according to claim 1, wherein the illuminating means comprise discrete wavelength light sources.

3. An optical sensor device according to claim 1, wherein the illuminating means comprise LEDs as light sources.

4. An optical sensor device according to claim 1, wherein the illuminating means comprise light sources emitting red, diffuse light with a wavelength of about 650 nm.

5. An optical sensor device according to claim 1, wherein the image recording means include cameras with objectives.

6. An optical sensor device according to claim 1, wherein the obliquely reflecting optical elements (25, 26) comprise agglutinated rectangular prisms with reflective coated hypotenuses extending in geometric planes which are skewed with respect to the intermediate geometrical plane (p1).

7. An optical sensor device according to claim 1, wherein each seat (14, 15) is provided with a fixed optical window (27, 28) providing an abutment surface for each electrode (E1, E2).

8. An optical sensor device according to claim 7, wherein the optical windows (27, 28) comprise sapphire windows.

9. An optical sensor device according to claim 1, wherein each opening (11, 11a) is provided with brush means (13) for preventing light and dust from entering the housing (10).

10. An optical sensor device according to claim 1, wherein
    the first illuminating means comprise two light sources (16, 17) arranged on opposite sides of a symmetry plane (p2) for projecting the first and second light beams (L1, L2) onto two sets of mirrors (18, 20, 21; and 19, 22, 23) so arranges as to reflect the first and second light beams on the two oblique reflecting elements (25, 26), and
    the image recording means comprise a single image recording means (31) oriented in the symmetry plane towards the two sets of mirrors so as to capture images (I1, I2) reflected back by the two oblique reflecting elements (25, 26) and the two sets of mirrors.

11. An optical sensor device according to claim 1, wherein the two sets of mirrors (18, 20, 21; and 19, 22, 23) are so arranged as to determine two luminous paths according to a closed polygonal line, whereby the first and second light beams (L1, 12) projected from the two light sources (16, 17) reach the two oblique reflecting elements (25, 26) which divert the two light beams (L1, L2) on each of the front faces of the electrodes (E1, E2).

12. An optical sensor device according to claim 1, wherein the first illuminating means comprise two light sources (16, 17), and the two oblique reflecting elements (25, 26) are arranged in an intermediate position between the two light sources (16, 17), whereby the two light beams (L1, L2) emitted from the light sources (16, 17) are aligned and directed toward one another, and wherein
    between each of the light sources (16, 17) and the oblique reflecting elements (25, 26) there is interposed a respective partially transparent reflecting element (18a, 19a) which leaves the respective light beam (L1, L2) coming directly from the light source (16, 17) filter towards the respective oblique reflecting element (25, 26) and reflects a front image (I1, I2) of the respective electrode (E1, E2), coming from the same oblique reflecting element (25, 26), towards a respective one of two image recording means (31, 131).

* * * * *